United States Patent [19]

Hammond et al.

[11] Patent Number: 5,597,900
[45] Date of Patent: Jan. 28, 1997

[54] CRYSTALLINE INTERLEUKIN-4

[75] Inventors: Gerald Hammond, East Orange; Hung V. Le, Rockaway; T. L. Nagabhushan, Parsippany; Paul Reichert, Montville; Paul P. Trotta, Secaucus, all of N.J.

[73] Assignee: Schering Corporation, Kenilworth, N.J.

[21] Appl. No.: 376,536

[22] Filed: Jan. 20, 1995

Related U.S. Application Data

[63] Continuation of Ser. No. 949,817, filed as PCT/US91/04045 Jun. 13, 1991, abandoned, which is a continuation-in-part of Ser. No. 538,636, Jun. 15, 1990, abandoned.

[51] Int. Cl.⁶ .................................................. C07K 14/54
[52] U.S. Cl. ...................... 530/351; 424/85.2; 435/69.52
[58] Field of Search .................. 424/85.2; 435/69.52; 530/351, 402, 408, 409, 512

[56] References Cited

U.S. PATENT DOCUMENTS 4,958,007  9/1990  Alroy et al. .......................... 435/69.52

FOREIGN PATENT DOCUMENTS 0254399  1/1958  European Pat. Off. .

OTHER PUBLICATIONS

Sano, C., et al J. Biol. Chem 4766 (1987).
Grabstein et al., J. Immunol. 139:1148 (1987).
Hu–Li et al., J. Exp. Med. 165:157 (1987).
Kimmenade et al., Eur. J. Biochem. 173:109 (1988).
McPherson, A., in Preparation and Analysis of Protein Crystals, 1982, John Wiley & Sons, New York, pp. 82–127.
Le et al., J. Biol. Chem. 263:10817 (1988).
McPherson, Scientific American Mar. 1989, pp. 62–69.
Protein Term and Function, ed. Bradshaw et al, 1990.
Protein Purification, ed. Scopes, 1987.
Prestle et al *EMBO* 7(2) 1988, pp. 339–343.
La Lande et al, *J Mol Biol.* 205, 1989, pp. 783–785.
Morega et al, Bio/Technology 4, 1986, pp. 904–905.

*Primary Examiner*—John Ulm
*Attorney, Agent, or Firm*—Paul G. Lunn; Norman C. Dulak

[57] ABSTRACT

A process for crystallizing recombinant human interleukin 4 (rhuIL-4) from a solution containing a sulfate or citrate salt is described. The crystalline form is suitable for x-ray diffraction and has wide applications in several pharmaceutical processes including purification, formulation and manufacturing.

6 Claims, No Drawings

CRYSTALLINE INTERLEUKIN-4

This is a continuation of application Ser. No. 07/949,817 filed Dec. 14, 1992, now abandoned, which is the United States national application corresponding to International Application No. PCT/US91/04045, filed Jun. 13, 1991 and designating the U.S., which PCT application is in turn a continuation-in-part of U.S. application Ser. No. 07/538636, filed Jun. 15, 1990, now abandoned, the benefit of which applications are claimed pursuant to the provisions of 35 U.S.C. §§120, 363 and 365(C).

BACKGROUND OF THE INVENTION

The T cell derived interleukin-4 (IL-4) was originally described as a murine factor that could co-stimulate the proliferation of activated B cells [Howard et al., J. Exp. Med. 155:914 (1982)]. Subsequently, it was demonstrated that murine IL-4 could exert a variety of biological effects on B cells [Paul et al., Ann. Rev. Immunol. 5:429 (1987); Noelle et.al., Proc. Natl. Acad. Sci. U.S.A. 81:6149 (1984); Roehm et al., J. Exp. Med. 160:679 (1984); Vitetta et al., J. Exp. Med. 162:1726 (1985); Coffman et al., J. Immunol. 136:4538 (1986); Coffman et al., J. Immunol. 136:949 (1986)] and other cell types including T cells [Mosmann et al., Proc. Natl. Acad. Sci. U.S.A. 83:5654 (1986); Fernandez-Botran et al., J. Exp. Med. 164:580 (1986); Hu-Li et al., J. Exp. Med. 165:157 (1987); Grabstein et al., J. Immunol. 139:1148 (1987); Zlotnick et al., Proc. Natl. Acad. Sci. U.S.A. 84:3856 (1987)], hematopoietic progenitor cells [Rennick et al., Proc. Natl. Acad. Sci. U.S.A. 84:6889 (1987); Peschel et al., Blood 70:254 (1987)] and mast cells (Mosmann, supra).

Based on homology with mudne IL-4, a cDNA encoding human interleukin-4 (huIL-4) has been cloned [Yokota et al., Proc. Natl. Acad. Sci. U.S.A. 83:5894 (1986)] and expressed in both mammalian [Le et al., J. Biol. Chem. 263:10817 (1988); Sonoda et al., J. Biotechnology 9:61 (1988); Takebe et al., Mol. Cell Biol. 8:466 (1988)] and bacterial [van Kimmenade et al., Eur. J. Biochem. 173:109 (1988)] hosts. Like murine IL-4, recombinant huIL-4 (rhuIL-4) is a pleiotropic lymphokine that acts on a variety of cell types. Thus, for example, rhuIL-4 can induce the proliferation of both activated T and B lymphocytes [Spits et al., J. Immunol. 139:1142 (1987); DeFrance et al., J. Immunol. 139:1135 (1987)], enhance the expression of class II major histocompatibility antigens and the low affinity receptor for IgE on B cells [Rousset et al., J. Immunol. 140:2625 (1988); DeFrance et al., J. Exp. Med. 165:1459 (1987)] and induce production of IgE and other immunoglobulins [Pene et al., Proc. Natl. Acad. Sci. U.S.A. 85:6880 (1988)]. The ability of rhuIL-4 to inhibit IL-2 dependent proliferation of chronic lymphocytic leukemic cells of B cell origin has suggested a clinical application in B cell neoplasms [Karray et al., J. Exp. Med. 168:85 (1988)].

The availability of milligram quantities of purified rhuIL-4 has facilitated the initiation of studies of the structure and the structure-function relationships of the protein. The present invention relates to the discovery of conditions for producing crystalline rhuIL-4. The invention further relates to the crystalline rhuIL-4 itself. The crystals are suitable for X-ray diffraction studies and have applications in the purification and formulation of rhuIL-4.

SUMMARY OF THE INVENTION

In its broadest aspect the invention relates to Interleukin-4 in crystalline form.

The invention further relates to human interleukin-4 in crystalline form.

The invention further relates to human interleukin-4 which has been produced by recombinant DNA techniques in crystalline form.

The invention further relates to interleukin-4 in crystalline form which may be glycosylated or non-glycosylated.

The invention further relates to a method for producing crystals of interleukin-4, which method comprises crystallizing interleukin-4 from a buffered pH 5–7 aqueous solution comprising a sulfate or citrate salt.

DESCRIPTION OF THE INVENTION

The crystalline interleukin-4 of this invention is useful for X-ray crystallographic analysis and for the preparation of pharmaceutical compositions for the treatment of any medical condition susceptible to treatment by interleukin-4.

To illustrate the practice of the present invention, the mature form of huIL-4 was expressed in $E.\ coli$. Other IL-4's as well as other forms of rhuIL-4 may similarly be utilized. Purification of rhuIL-4 from the cell supernatant was accomplished by conventional chromatographic methods (Le et al., supra). Hanging drop vapor diffusion experiments were performed in 24-well tissue culture plates (Multiwell, Becton Dickenson & Co, Lincoln Park, N.J.). Droplets (6 µL) containing 20 mg/ml of huIL-4, 15–20% saturated ammonium sulfate, 40 mM sodium phosphate, pH 6.0–7.0, were hung from siliconized coverslips inverted into 24-well tissue culture plates. These droplets were equilibrated at either 12° or 22° C. against 1 ml of 30–40% saturated ammonium sulfate, 40 mM sodium phosphate, pH 6.0–7.0. Controlled temperature incubation was performed in REVCO environmental chambers preset at 12° or 22° C.

The concentration of rhuIL-4 in various buffers was determined spectrophotometrically using an extinction coefficient of 0.57/cm/mg/ml at 278 nm. Sodium dodecylsulfate polyacrylamide gel electrophoresis (SDS-PAGE) was performed according to the method of Laemmli [Nature 227:680 (1970)]. Reversed phase HPLC was performed on a Rainin C4 column (4.6×250 nm; Dynamax, 300 Angstrom) developed with a linear gradient of acetonitrile in 0.1% trifluoroacetic acid. Determination of T cell proliferation activity using human peripheral blood lymphocytes was performed as described previously (Yokota et al., supra). For X-ray studies, large tetragonal crystals were mounted in glass capillaries and photographed with a precession camera at 22° C. using CuKα radiation from a Rigaku RU-300 rotating anode. A complete native data set was collected on a Nicolet X-100A area detector using the same radiation source.

As previously stated, for purposes of illustration, the crystalline human interleukin-4 described in this invention is recombinant human interleukin-4 derived from $E.\ coli$. The primary structure of the protein is:

```
    1 H K C D I T L Q E I I K T L N S L T E Q K T L C T E L T V T
   31 D I F A A S K N T T E K E T F C R A A T V L R Q F Y S H H E
```

```
 61  K D T R C L G A T A Q Q F H R H K Q L I R F L K R L D R N L

91  W G L A G L N S C P V K E A N Q S T L E N F L E R L K T I M

121  R E K Y S K C S S
```

Using ammonium sulfate as precipitant rhuIL-4 has been crystallized into needles and large tetragonal crystals. Crystallization may best be achieved in 40 mM sodium phosphate buffer, pH 6.0, containing 34% ammonium sulfate, after 21 days of incubation at 12° C. The tetragonal crystals have also been observed in sodium phosphate at pH values ranging from 5.0 to 7.0 and at concentrations of ammonium sulfate ranging from 30 to 40% saturation.

Crystallization is carried out at a pH range of 5 to 7, preferably 5.5 to 6.5 and most preferably at about pH 6.0. The temperature can range from about 5° to 25° C., preferably from 12° to 22° C. and most preferably will be about 12° C. The protein concentration at equilibrium should be from about 5 to 60 mg/ml, preferably 30 to 50 mg/ml and most preferably about 40 mg/ml.

The period of incubation at 12° C. to 22° C. can vary from 2 to 20 days. It is anticipated that the crystallization methods described herein will also be useful for the crystallization of rhuIL-4 derived from other host cells (e.g. mammalian cells in culture, yeast, insects and others) or huIL-4 derived from natural sources (e.g., human peripheral blood lymphocytes or human cell lines constitutively producing huIL-4). It is also anticipated that the method will be applicable to homologous interleukin 4 proteins derived from other species.

Crystalline rhuIL-4 from the hanging droplets has been isolated and washed thoroughly in 55% ammonium sulfate, 40 mM sodium phosphate buffer, pH 6.6 at ambient temperature (22°–25° C.). After redissolution in 20 mM sodium phosphate buffer, pH 7.4, with 0.15M sodium chloride, the crystals exhibited T cell proliferation activity ($2.0 \times 10^7$ units/mg) which was identical to that of a control rhuIL-4 sample that had not been crystallized. When subjected to SDS-PAGE, the electrophoretic migration of the redissolved rhuIL-4 crystals was identical to that of the control sample. Similarly, the reversed phase HPLC elution pattern of the redissolved crystals was indistinguishable from the elution pattern of the control sample. No protein degradation was apparent as a result of the long period of incubation at 22° C. More importantly, the process of crystallization followed by redissolution in physiological buffer failed to inactivate the T cell proliferation activity of rhuIL-4.

X-ray diffraction data were initially collected to 2.7 Å resolution using the area detector. Oscillation frames covered 0.25 and were measured for 10 minutes. Indexing and integration of intensity data were carried out using the XENGEN processing programs [Howard et al., J. Appl. Crystallogr. 20:383 (1987)]. The data indexed in the tetragonal system; with a=92.1 (2), b=92.1 (7) and c=46.5 (1) Å. The space group is either $P4_2 2_1 2$ or $P4_3 2_1 2$.

Subsequent X-ray precession photographs of interleukin-4 confirmed the space group and unit cell parameters. The tetragonal crystals are stable to x-rays and diffract at room temperature for at least five days and diffract to at least 2.7 Å resolution.

Large scale crystallization can be accomplished by methods equivalent to vapor diffusion, namely, dialysis and ultrafiltration. Seed crystals obtained from a hanging drop experiment can be used to accelerate the large scale crystallization once the optimum conditions have been established. Although the use of ammonium sulfate as a precipitant is preferred, it can be replaced by other common sulfate and citrate salts such as sodium, potassium, calcium or magnesium sulfate; sodium citrate, and others (McPherson, Preparation and Analysis of Protein Crystals, 1982, John Wiley & Sons, New York, N.Y.). Large scale crystallization of rhuIL-4 can be introduced as a final purification step and/or concentration step in clinical manufacturing. Long term storage of rhuIL-4 bulk drug in a crystalline form is also highly desirable because of the inherent stability of the crystals as compared to rhuIL-4 stored in solution with preservatives.

The crystals prepared by the described method also constitute a particularly advantageous form for pharmaceutical dosage form preparation. The crystals may be used, for example, as a basis for a slow-release formulation of rhuIL-4 in vivo. It is believed that complexes of metals (e.g. zinc or iron) and huIL-4 could be formed and then subsequently crystallized. Crystals of these complexes could also be used in slow-release protein formulations containing appropriate pharmaceutical additives. Examples of similar slow-release protein formulations are the zinc-insulin crystalline complex (Remington's Pharmaceutical Sciences, 1985, Gennaro, A. R., Ed., Mack Publishing Co., Fasten, Pa., pp. 974–976) and the zinc-insulin-protamine crystalline complex (Pharmaceutical Manufacturing Encyclopedia, 1989, Sittig, M., Ed., pp. 820–821).

Slow-release pharmaceutical compositions comprising the crystalline interleukin-4 of the invention can be prepared by admixing such interleukin-4 with a metal and/or protein complexing agent as described above.

We claim:

1. Crystalline human, non-glycosylated interleukin-4.

2. The crystalline interleukin-4 of claim 1 that is produced by recombinant DNA techniques.

3. A method for producing crystals of interleukin-4 which comprises equilibrating a first solution comprised of an aqueous buffered solution of interleukin-4 having pH 5–7 and having a concentration of ammonium sulfate of 15%–20% at a temperature of 12° to about 22° C. against a second buffered solution having a 30–40% concentration of ammonium sulfate, pH 6.0–7.0 and having a concentration of interleukin-4 at equilibrium of from about 5 to 60 milligrams of interleukin-4 per milliliter of aqueous solution for a sufficient time to allow crystals of interleukin-4 to form and wherein the first and second buffered solutions are buffered with a phosphate buffer.

4. The method of claim 3 in which the concentration of interleukin-4 is from 30 to 50 mg/ml.

5. The method of claim 3 in which the concentration of interleukin-4 is 40 mg/ml.

6. Crystalline interleukin-4 produced by the process of claim 3.

* * * * *